US006730685B1

(12) United States Patent
Brülls

(10) Patent No.: US 6,730,685 B1
(45) Date of Patent: May 4, 2004

(54) FORMULATION OF SUBSTITUTED BENZIMIDAZOLES

(75) Inventor: Mikael Brülls, Kungälv (SE)

(73) Assignee: AstraZeneca AB, Sodertalje (SE)

(*) Notice: Subject to any disclaimer, the term of this patent is extended or adjusted under 35 U.S.C. 154(b) by 0 days.

(21) Appl. No.: 09/701,714

(22) PCT Filed: Oct. 13, 2000

(86) PCT No.: PCT/SE00/01992

§ 371 (c)(1),
(2), (4) Date: Dec. 1, 2000

(87) PCT Pub. No.: WO01/28558

PCT Pub. Date: Apr. 26, 2001

(30) Foreign Application Priority Data

Oct. 22, 1999 (SE) .............................. 9903831

(51) Int. Cl.$^7$ .................. A61K 31/44; A61K 31/415
(52) U.S. Cl. ........................ 514/339; 514/398
(58) Field of Search .................. 514/339, 398

(56) References Cited

U.S. PATENT DOCUMENTS

| 4,758,579 A | 7/1988 | Kohl et al. | 514/338 |
| 5,589,491 A | 12/1996 | Nakanishi et al. | 514/338 |
| 5,635,520 A | 6/1997 | Uda | 514/338 |
| 5,840,737 A | 11/1998 | Phillips | 514/338 |
| 5,877,205 A | 3/1999 | Andersson | 514/449 |
| 5,900,419 A | 5/1999 | Hausheer et al. | 514/282 |
| 6,207,188 B1 | 3/2001 | Gustavsson et al. | 424/464 |

FOREIGN PATENT DOCUMENTS

| EP | 0005129 | 4/1981 |
| EP | 0124495 | 1/1987 |
| EP | 0174726 | 4/1989 |
| EP | 0166287 | 8/1989 |
| EP | 0356143 | 1/1994 |
| EP | 0444625 | 6/1994 |
| GB | 2163747 | 3/1986 |
| WO | 9402141 | 2/1994 |
| WO | 9427988 | 12/1994 |

Primary Examiner—Raymond Henley, III
(74) Attorney, Agent, or Firm—White & Case LLP

(57) ABSTRACT

The present invention relates to stable liquid formulations that comprise a water free or almost water free, polyethylene glycol solution of sodium or potassium salt of a $H^+$, $K^+$-ATPase inhibitor of Formula I or a sodium or potassium salt of one single enantiomer thereof. Alternatively, the sodium or potassium salt of the $H^+$, $K^+$-ATPase inhibitor may be formed in situ in the polyethylene glycol solution by adding sodium or potassium hydroxide together and the active compound. The invention is also directed to the preparation of the claimed formulation, use of the stable liquid formulations in medicine and in the treatment of gastrointestinal diseases.

15 Claims, No Drawings

FORMULATION OF SUBSTITUTED BENZIMIDAZOLES

This is a 371 of PCT/SE00/01992 filed Oct. 13, 2000.

FIELD OF THE INVENTION

The present invention relates to a stable liquid formulation comprising an acid labile substituted benzimidazole compound such as a proton pump inhibitor, i.e. a $H^+$, $K^+$-ATPase inhibitor. The liquid product can be stored refrigerated or stored at room temperature for several months without significant degradation. The invention provides a stable liquid formulation of the $H^+$, $K^+$-ATPase inhibitor in a water free or almost water free solvent. Such a stable liquid formulation is i.a. suitable as a ready-to-use solution for parenteral administration or as a concentrate for ex tempore preparation of a solution for parenteral administration. Further, the present invention also refers to the manufacture of such stable liquid i.a. parenteral formulations, and their use in medicine.

BACKGROUND OF THE INVENTION AND PRIOR ART

The susceptibility for chemical degradation of the proton pump inhibitors poses special problems in the pharmaceutical formulation of solutions for parenteral administration. The degradation of the proton pump inhibitors in liquid solutions is pH-dependent; the rate of reaction is very high at low pH values.

The proton pump inhibitors have a low solubility in water and a higher solubility in less polar solvents. On the other hand, alkaline salts of the proton pump inhibitors generally have a higher solubility in water and a lower solubility in less polar solvents.

At present pharmaceutical formulations of proton pump inhibitors for parenteral administration are formulated as dry preparations for ex tempore reconstitution in a sterile solvent. The dry preparations are obtained by lyophilisation of sterile filtered solutions. The chemical instability of the proton pump inhibitors precludes heat sterilisation of these compounds.

Thus, at the same time as an enhanced solubility of the active compound is requested for parenteral administration, the stability of the formulations must be maintained and the formulations should have suitable storage stability. Further suitable requirements are easy handling and inexpensive manufacturing.

Proton pump inhibitors are for instance compounds known under the generic names omeprazole, lansoprazole, pantoprazole, rabeprazole, leminoprazole and esomeprazole. Omeprazole and therapeutically acceptable salts thereof are described in EP-A1-0005129. EP-A1-124495 describes certain salts of omeprazole and EP-A1-174726, EP-A1-166287 and GB 2163747 are directed to lansoprazole, pantoprazole and rabeprazole respectively. WO 94/27988 is directed to salts of the single enantiomers of omeprazole.

Proton pump inhibitors are susceptible to degradation/transformation in acidic and neutral media. Due to the stability problems, intravenous formulations of the $H^+$, $K^+$-ATPase inhibitors are usually made in the form of a dry powder that is to be dissolved in a liquid just before use.

For instance, WO 94/02141 describes an injection of an antiulcerative benzimidazole compound, such as omeprazole. The injection comprises a lyophilised product, which is dissolved in physiological saline just before use. The lyophilised product is prepared from a strong alkaline solution of sodium salt of omeprazole, sodium hydroxide and water, whereafter the solution is lyophilised.

EP 356 143-A1 describes an injectable solution comprising a substituted benzimidazole and at least one of ethanol, propylene glycol and polyethylene glycol. The active compound is either used as such, or preferably as a lyophilised material of an alkaline aqueous solution of the compound, dissolved in the ethanol, propylene or polyethylene glycol. If a lyophilised material is used an acidic substance is also added to the solvent. The examples in Table 2 (EP 356143-A1, page 5) comprising polyethylene glycol have a water content of about 50%.

EP 124 495 describes for instance, see example 13, injectable solutions which are obtained by dissolving omeprazole sodium salt in sterilised water, followed by filtration and lyophilisation to give a lyophilised material. The prepared material is then dissolved in a sterile-filtered mixed solution of polyethylene glycol 400 for injection, sodium dihydrogenphosphate and sterilised water.

The previously described parenteral dosage forms recommend a freeze dried product, which makes the manufacture of intravenous products expensive. The present invention provides a stable liquid formulation which can be used as a ready-to-use solution for parenteral administration or a concentrate for ex tempore preparation of a solution for parenteral administration without using lyophilisation processes/steps in the manufacturing.

SUMMARY OF THE INVENTION

The present invention provides a stable liquid formulation of an acidic susceptible $H^+K^+$-ATPase inhibitor, such as a proton pump inhibitor. The stable liquid formulation can be used as a ready-to-use solution for parenteral administration or as a concentrate for ex tempore preparation of a solution for parenteral administration. The liquid product can be stored refrigerated or stored at room temperature for several months without significant degradation.

According to one aspect of the present invention a water free or almost water-free, polyethylene glycol solution of a sodium or potassium salt of a $H^+,K^+$-ATPase inhibitor of Formula I below or a sodium or potassium salt of a single enantiomer of one of the compounds is provided.

According to another aspect, the sodium or potassium salt of the $H^+$, $K^+$-ATPase inhibitor may be formed in situ in the polyethylene glycol solution by adding a sodium hydroxide or potassium hydroxide and the active compound, i.e. the $H^+$, $K^+$-ATPase inhibitor.

Water that has been added with the sodium or potassium salt of the active compound or that has been formed by the in situ formation of the sodium or potassium salt of the active compound, can be evaporated by purging the polyethylene glycol solution with nitrogen. It is by such a procedure possible to remove practically all the water or to obtain a water content of a pre-set value.

Alternatively, the stable liquid formulation may also be filled into capsules which then are enteric coated, and used for oral administration.

According to a further aspect the stable liquid formulation may be filled into a one or two compartment syringe to provide a ready-to-use product or ex tempore preparation product that will be easy to use for parenteral administration.

DETAILED DESCRIPTION OF THE INVENTION

Compounds of interest for the novel stable liquid formulation according to the present invention are a sodium or potassium salt of compounds with the general formula I $$Het_1—X—\overset{\overset{O}{\|}}{S}—Het_2 \quad I$$

wherein

Het$_1$ is

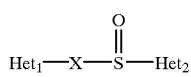

Het$_2$ is

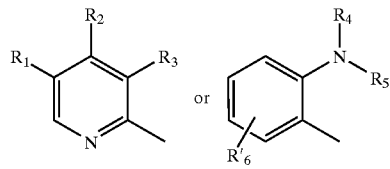

X =

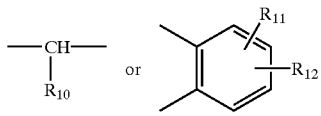

wherein

N in the benzimidazole moiety means that one of the ring carbon atoms substituted by R$_6$-R$_9$ optionally may be exchanged for a nitrogen atom without any substituents;

R$_1$, R$_2$ and R$_3$ are the same or different and selected from hydrogen, alkyl, alkoxy optionally substituted by fluorine, alkylthio, alkoxyalkoxy, dialkylamino, piperidino, morpholino, halogen, phenyl and phenylalkoxy;

R$_4$ and R$_5$ are the same or different and selected from hydrogen, alkyl and aralkyl;

R$_6$' is hydrogen, halogen, trifluoromethyl, alkyl and alkoxy;

R$_6$–R$_9$ are the same or different and selected from hydrogen, alkyl, alkoxy, halogen, haloalkoxy, alkylcarbonyl, alkoxycarbonyl, oxazolyl, trifluoroalkyl, or adjacent groups R$_6$–R$_9$ form ring structures which may be further substituted;

R$_{10}$ is hydrogen or forms an alkylene chain together with R$_3$ and

R$_{11}$ and R$_{12}$ are the same or different and selected from hydrogen, halogen or alkyl.

Examples of specifically interesting compounds are a sodium or potassium salt of the following compounds with formula I

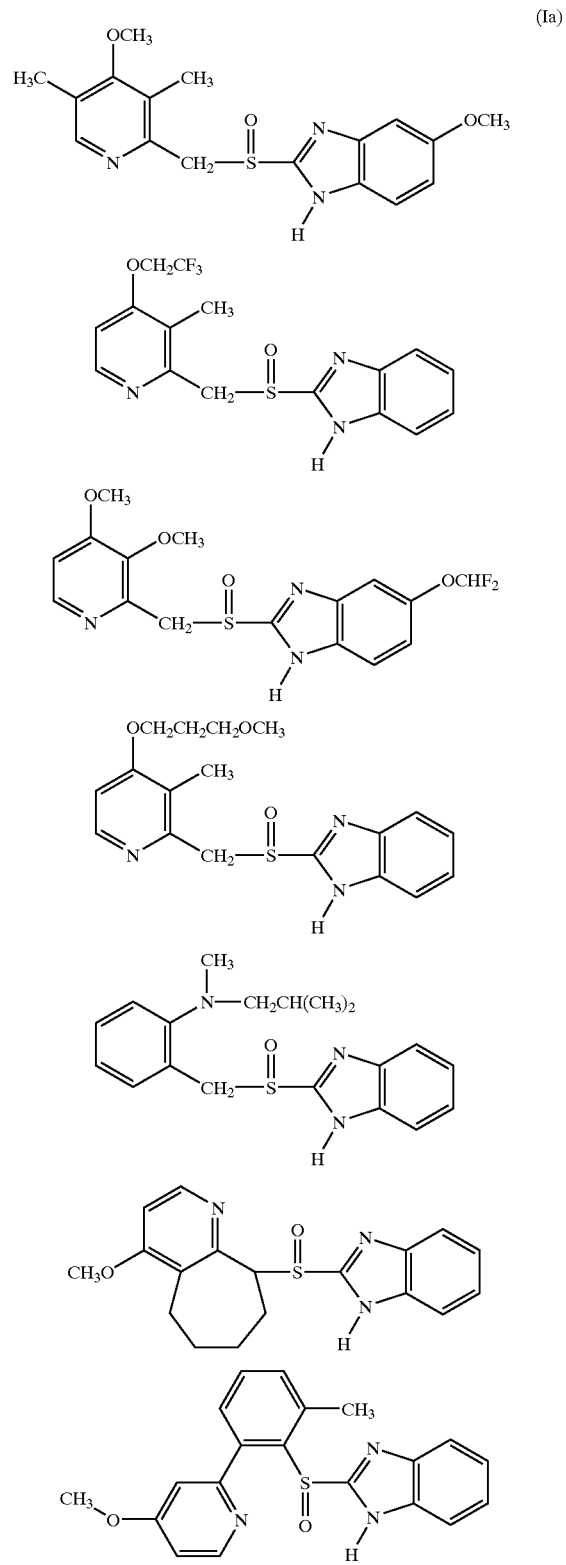

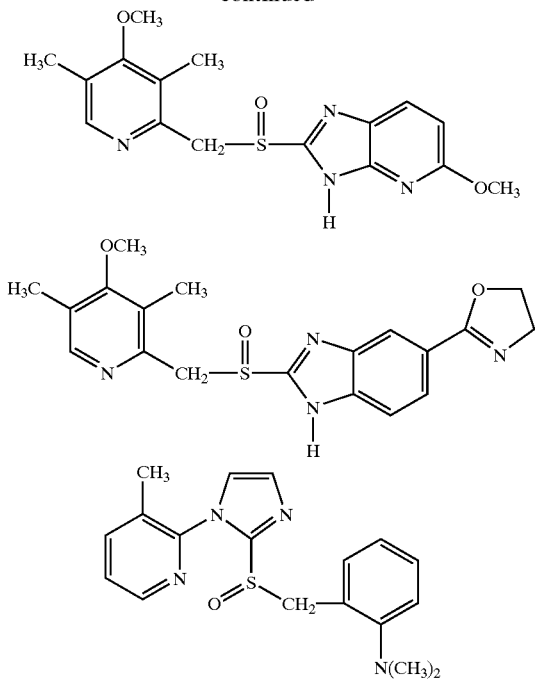

The compounds may also be used in the form of a sodium or potassium salt of a single enantiomer. Especially preferred compounds for the present invention are a sodium salt of omeprazole or a sodium salt of (S)-omeprazole.

The stable liquid formulation is prepared by dissolving a sodium or potassium salt of a compound with Formula I in polyethylene glycol. Suitable polyethylene glycols are for instance, polyethylene glycol 200, 300 or 400. The most preferred polyethylene glycol is PEG 400. There is no need for any addition of water to the PEG solution. The prepared formulation according to present invention is water free or almost water free. The formulation should comprise less than 6% by weight of water, preferably less than 3%, and more preferably less than 2% by weight of water.

Water that has been added with the sodium or potassium salt of the active compound or that has been formed by the in situ formation of the sodium or potassium salt of the active compound, can be evaporated by purging the polyethylene glycol solution with nitrogen. It is by such a procedure possible to remove practically all the water or to obtain a water content of a pre-set value.

Alternatively, the compound of Formula I can be used as such added and dissolved together with at least an equivalent amount of sodium or potassium hydroxide in polyethylene glycol. The sodium salt or potassium salt of the active compound will then be formed in situ.

It is of vital importance that the formulation contains the active compound in the form of a sodium or potassium salt in order to obtain a stable product.

The water solubility of proton pump inhibitor compounds is low and they are generally more soluble in less polar solvents. The solubility of proton pump inhibitors in polyethylene glycol is as expected in general higher than the corresponding water solubility. It has now been discovered that a sodium or potassium salt of the active $H^+,K^+$-ATPase inhibitor surprisingly has a higher solubility in polyethylene glycol than the active compound itself. It is therefore possible to achieve a high concentration of the compound in the polyethylene glycol solution with a sodium or potassium salt of the active compound. A high concentration is of vital importance particularly for parenteral products since the volume to be administered is generally small. The injection volume for an intravenous bolus injection should preferably not exceed 10 ml and for a subcutaneous injection the volume should preferably not exceed 1 ml.

Water that has been added with the sodium or potassium salt of the active compound or that has been formed by the in situ formation of the sodium or potassium salt of the active compound can be evaporated by purging the polyethylene glycol solution with nitrogen. It is by such a procedure possible to remove practically all the water or to obtain a water content of a pre-set value.

An advantageous feature of the stable liquid formulation of the invention is that it can be filtrated sterile by conventional methods and it is therefore relatively easy to produce a sterile parenteral product aseptically.

The stable liquid formulation may be filled into a one or two compartment syringe to provide a ready-to-use product or ex tempore preparation product that will be easy to use for parenteral administration.

The stable liquid formulation may be mixed with for instance water for injection or saline solution for injection when it is used as a concentrate for ex tempore preparation for parenteral administration. The solvent may also comprise a pharmaceutically acceptable excipient that will control the pH of the final solution to a desired value. If the stable liquid formulation is to be filled into one of the chambers of a two compartments syringe, the other chamber in the syringe will then be filled with a suitable solvent as described above. This syringe will then become an easy to use ex tempore preparation product in contrast to earlier proposed arrangements. For instance, a product according to prior art, a two compartments syringe, would contain the lyophilised $H^+,K^+$-ATPase in one compartment and a sterile water solution in the other compartment. Such a structural arrangement would lead to a very expensive method of manufacture compared to the invention provided in this patent application.

The stable liquid formulation according to the present invention may comprise suitable pharmaceutically acceptable excipients that can be dissolved in the water free or almost water free polyethylene glycol formulation without interferring with the properties and uses of the claimed formulation, such as stability and solubility.

Use of the Invention

The pharmaceutical substances used in the claimed formulations are useful for inhibiting gastric acid secretion in mammals including man by controlling gastric acid secretion at the final step of the acid secretory pathway and thus reduce basal and stimulated gastric acid secretion irrespective of stimulus. In a more general sense, they may be used for prevention and treatment of gastric-acid related diseases in mammals and man, including e.g. reflux oesophagitis, gastritis, duodenitis, gastric ulcer, duodenal ulcer and Zollinger-Ellison syndrom. Furthermore, they may be used for treatment of other gastrointestinal disorders where gastric acid inhibitory effect is desirable e.g. in patients treated with non-steroidal anti-inflammatory drugs (NSAID), in patients with Non Ulcer Dyspepsia, and in patients with symptomatic gastro-oesophageal reflux disease (GORD). They may also be used for patients in intensive care situations, in patients with acute upper gastrointestinal bleeding, pre-and postoperatively to prevent aspiration of gastric acid and to prevent and treat stress ulceration. Further, they may be useful in the treatment of psoriasis as well as in the treatment of Helicobacter infections and diseases related to these.

A unit dose of the proton pump inhibitor, for instance 1–100 mg is preferably administered once or twice a day. The doses may be given with a higher dosing frequency depending on the severeness of the disease and the patient's conditions, also up to 500 mg may be adminstered per day in severere cases. Suitable doses for injection and infusion comprise for instance 5, 10, 15, 20, 30 and 40 mg of the pharmaceutical active compound.

The formulations may also be used in combination with other drug treatments, such as one or more antibacterial compounds, a motility stimulating drug, an antacid and/or a $H_2$-blocker, such as for instance ranitidine.

The following examples show the preparation of stable liquid formulations comprising the sodium salt of omeprazole and polyetylene glycol 400. These formulations were compared with other formulations, and the results show the enhanced stability and solubility of the claimed stable liquid formulations.

EXAMPLES

Example 1

Stable Liquid Formulation of Omeprazole

Liquid formulations of omeprazole or sodium omeprazole in water or polyethylene glycol 400 were prepared and analysed after different storage times at room temperature (25° C.). Formulations A–D were prepared by dissolving omeprazole sodium monohydrate in polyethylene glycol 400 and then purging the solutions with nitrogen in order to remove any water that had been added with the active compound. To solution D was then also added 2% water. Formulation E was prepared by dissolving omeprazole (non salt form) in polyethylene glycol and then purging the solution with nitrogen in order to remove any water that had been added with the active compound. Formulation F was prepared by dissolving omeprazole sodium monohydrate in water.

Aliquots of 0.5 ml of each of the solutions were filled in 3 ml glass vials and sealed with rubber stoppers. Formulation B was sealed under dry air and all of the other formulations were sealed under nitrogen. The appearance of the solutions were determined after different storage times.

As shown in Table 1, the polyethylene glycol solutions containing omeprazole sodium (formulations A–D) remained clear and colourless or almost colourless during the studied storage period. This shows that the stability of omeprazole sodium was very good in the polyethylene glycol solutions. Formulations E and F were intensely discoloured and precipitation was formed within the studied storage period. This shows that the stability of omeprazole in the polyethylene glycol solution (formulation E) was poor and that the stability of omeprazole sodium in the water solution (formulation F) was poor. It can also be concluded that the polyethylene glycol solutions with omeprazole sodium was not sensitive to oxygen in the head space (formulation B) nor to a small water content (formulation C).

TABLE 1

Appearance of different omeprazole formulations, stored at 25° C.

| Formulation | A (invention) | B (invention) | C (invention) | D (invention) | E | F |
| --- | --- | --- | --- | --- | --- | --- |
| Added substance | Omeprazole sodium salt | Omeprazole sodium salt | Omeprazole sodium salt | Omeprazole sodium salt | Omeprazole | Omeprazole sodium salt |
| Omeprazole content (mg/g) | 70 | 70 | 69 | 14 | 13 | 80 |
| Solvent | PEG400 | PEG400 | PEG400 | PEG400 | PEG400 | Water |
| Amount added water | None | None | 2% (by weight) | None | None | 100% |
| Head space in vial | Nitrogen | Air | Nitrogen | Nitrogen | Nitrogen | Nitrogen |
| Storage time (months) | Appearance | | | | | |
| 0 | Clear colourless solution | Clear colourless solution | Clear colourless solution | Clear colourless solution | Clear colourless solution | Clear colourless solution |
| 1.2 | n.d. | n.d. | n.d. | n.d. | n.d. | Yellow solution with brown precipitation |
| 1.7 | Clear colourless solution | Clear colourless solution | Clear colourless solution | Clear colourless solution | Deep red solution with precipitation | n.d. |

TABLE 1-continued

Appearance of different omeprazole formulations, stored at 25° C.

| Formulation | A (invention) | B (invention) | C (invention) | D (invention) | E | F |
|---|---|---|---|---|---|---|
| 3.5 | Clear slightly yellow solution | Clear slightly yellow solution | Clear slightly yellow solution | Clear colourless solution | n.d. | Brown yellow solution with heavy purple precipitation | n.d. = not determined

Example 2

Solubility of Omeprazole and Omeprazole Sodium in Polyethylene Glycol

The solubility of omeprazole (the non-ionised species) has been determined to approximately 0.1 g/l in water and approximately 100 g/l in dichloromethane at room temperature (22° C.).

This means that the solubility of omeprazole is much better in dichloromethane, a less polar solvent, than in water.

Omeprazole sodium on the other hand is freely soluble in water and only slightly soluble in dichloromethane and this, again, is due to the large differences in polarity of the different solvents. Omeprazole sodium is ionised and is therefore much more soluble in water compared with omeprazole and the opposite is applicable in the less polar solvent dichloromethane.

The solubility of omeprazole (the non-ionised species) has been determined to approximately 20 g/l in polyethylene glycol 400. This means that the solubility is much better in polyethylene glycol, a less polar solvent, than in water.

Omeprazole sodium is freely soluble in polyethylene glycol 400, which is unexpected and contradictory to what was expected. This means that the solubility in polyethylene glycol is much higher for omeprazole sodium than for omeprazole. The high solubility of omeprazole sodium in polyethylene glycol is very favourable regarding the formulation aspects of a parenteral pharmaceutical product.

What is claimed is:

1. A water free or almost water free, stable liquid formulation comprising polyethylene glycol and a sodium or potassium salt of a $H^+$, $K^+$-ATPase inhibitor, and optionally pharmaceutically acceptable excipients that are soluble in the formulation.

2. The stable liquid formulation according to claim 1, wherein the sodium or potassium salt of the $H^+$,$K^+$-ATPase inhibitor is a sodium or potassium salt of a compound with the general formula I, or a sodium or potassium salt of the single enantiomer thereof

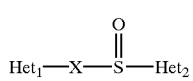

I wherein
$Het_1$ is

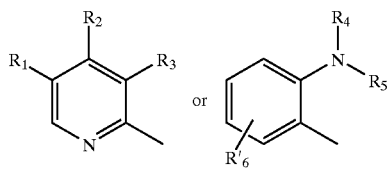

$Het_1$ is

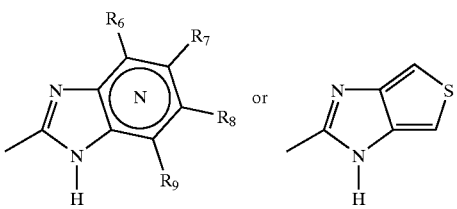

B=

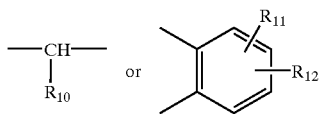

wherein
N in the benzimidazole moiety means that one of the ring carbon atoms substituted by $R_6$–$R_9$ optionally may be exchanged for a Ditrogen atom without any substituents;
$R_1$, $R_2$ and $R_3$ are the same or different and selected from the group consisting of hydrogen, alkyl, alkoxy unsubstituted or substituted by fluorine, alkylthio, alkoxyalkoxy, dialkylamino, piperidino, morpholino, halogen, phenyl and phenylalkoxy;
$R_4$ and $R_5$ are the same or different and selected from the group consisting of hydrogen, alkyl and arylalkyl;
$R_6'$ is selected from the group consisting of hydrogen, halogen, trifluoromethyl, alkyl and alkoxy,
$R_6$–$R_9$ are the same or different and selected from the group consisting of hydrogen, alkyl, alkoxy, halogen, haloalkoxy, alkylcarbonyl, alkoxycarbonyl, oxazolyl, and trifluoroalkyl, or adjacent groups $R_6$–$R_9$ form ring structures which may be ether substituted;
$R_{10}$ is hydrogen or forms an alkylene chain together with $R_3$; and
$R_{11}$ and $R_{12}$ are the same or different and selected from the group consisting of hydrogen, halogen and alkyl.

3. The stable liquid formulation according to claim 2, wherein the sodium or potassium salt of the $H^+$,$K^+$-ATPase inhibitor is the sodium or potassium salt of a compound with any of the following formulas, or the sodium or potassium salt of the single enantiomer thereof

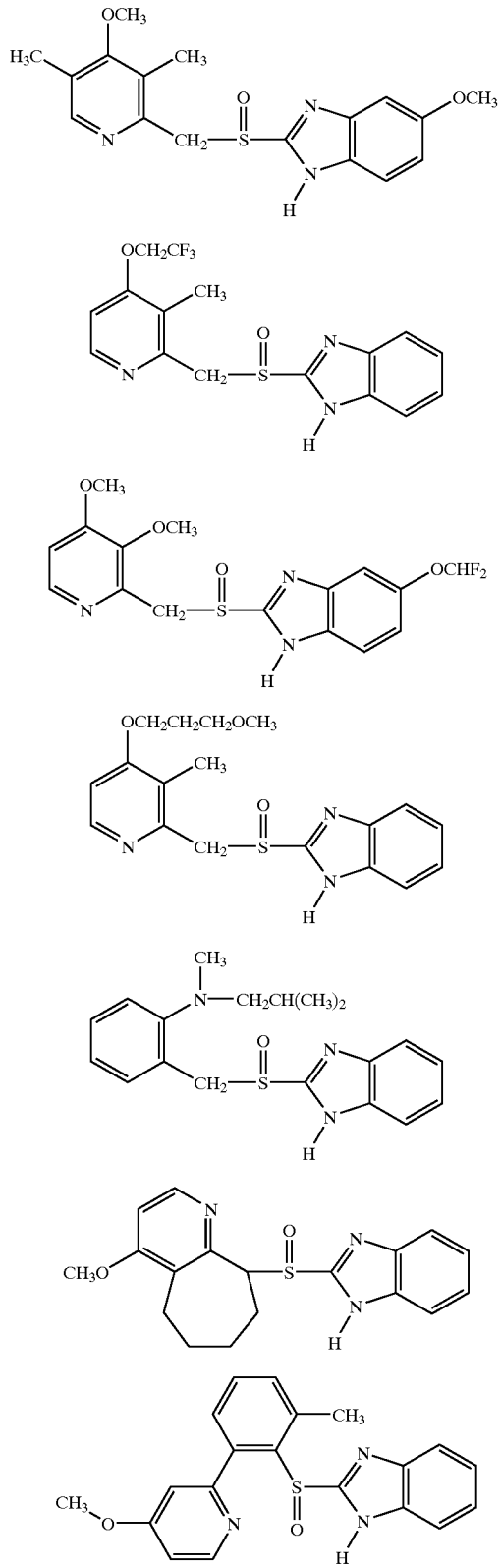

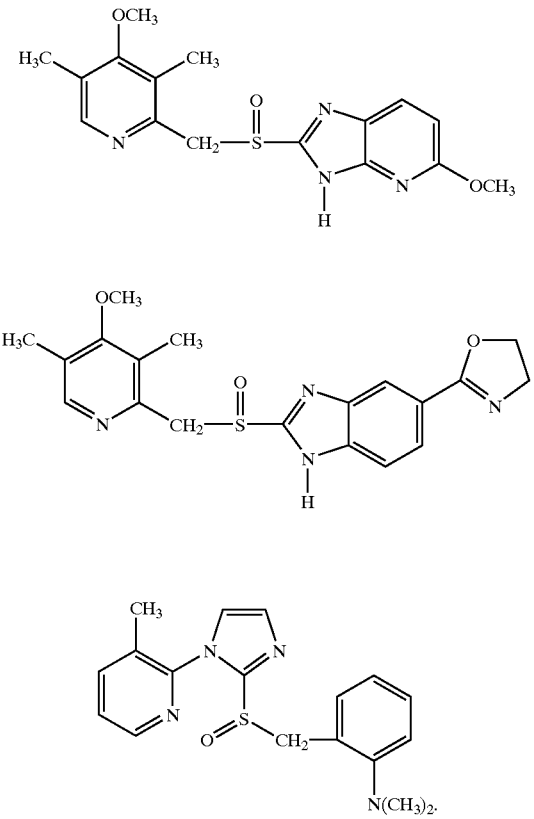

4. The stable liquid formulation according to any of claims 1–3, wherein the compound is a sodium salt.

5. The stable liquid formulation according to any of claims 1–3, wherein the compound is a potassium salt.

6. The stable liquid formulation according to claim 4, wherein the compound is the sodium salt of (S)-omeprazole or the sodium salt of omeprazole.

7. The stable liquid formulation according to any of claims 1—3, wherein the polyethylene glycol is selected from polyethylene glycol 200, 300 and 400.

8. The stable liquid formulation according to claim 7, wherein the polyethylene glycol is polyethylene glycol 400.

9. The stable liquid formulation according to any of claims 1—3, wherein the water content of the solution is less than 6% by weight.

10. The stable liquid formulation according to claim 9, wherein the water content is less than 3% by weight.

11. The stable liquid formulation according to claim 10, wherein the water content is less than 2% by weight.

12. A process for the preparation of a water free or a most water free stable liquid formulation comprising polyethylene glycol and a sodium or potassium salt of a $H^+,K^{30}$-ATPase inhibitor, and optionally pharmaceutically acceptable excipients that are soluble in the formulation, wherein the sodium or potassium salt of the $H^+,K^+$-ATPase inhibitor and polyethylene glycol are mixed, and optional excipients are added, whereafter the solution optionally is purged with nitrogen to obtain a water content of a pre-set value.

13. A process for the preparation of a water free or almost water free stable liquid formulation comprising polyethylene glycol and a sodium or potassium salt of a $H^+,K^{30}$-ATPase inhibitor, and optionally pharmaceutically acceptable excipients that are soluble in the formulation, wherein the $H^+,K^+$-ATPase inhibitor, sodium or potassium hydroxide and polyethylene glycol are mixed, and optional excipients are added, whereafter the solution optionally is purged with nitrogen to obtain a water content of a pre-set value.

14. The process according to claim 11 or 12, wherein the process further comprises the step that the liquid formulation is sterile filtered.

15. A method for treating gastrointestinal diseases wherein a therapeutically effective amount of a stable liquid formulation according to any of claims 1—3 is administered to a subject in need thereof.

* * * * *

UNITED STATES PATENT AND TRADEMARK OFFICE
CERTIFICATE OF CORRECTION

PATENT NO. : 6,730,685 B1 Page 1 of 1
DATED : May 19, 2004
INVENTOR(S) : Mikael Brülls It is certified that error appears in the above-identified patent and that said Letters Patent is hereby corrected as shown below:

Column 10,
Line 24, "$Het_1$" should read -- $Het_2$ --.
Line 35, "B=" should read -- X= --.
Line 46, "Ditrogen" should read -- nitrogen --.
Line 60, "ether" should read -- further --.

Column 12,
Line 53, "a most" should read -- almost --.
Lines 55 and 64, "$K^{30}$" should read -- $K^+$ --.

Column 13,
Line 4, "11 or 12" should read -- 12 or 13 --.

Signed and Sealed this

Sixth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,730,685 B1  
APPLICATION NO. : 09/701714  
DATED : May 19, 2004  
INVENTOR(S) : Mikael Brülls Page 1 of 1

It is certified that error appears in the above-identified patent and that said Letters Patent is hereby corrected as shown below:

In column 12, line 64: "$K^{30}$" should read read --$K^+$--.

Signed and Sealed this

Twenty-ninth Day of August, 2006

JON W. DUDAS  
*Director of the United States Patent and Trademark Office*

UNITED STATES PATENT AND TRADEMARK OFFICE
CERTIFICATE OF CORRECTION

PATENT NO. : 6,730,685 B1
APPLICATION NO. : 09/701714
DATED : May 4, 2004
INVENTOR(S) : Mikael Brülls It is certified that error appears in the above-identified patent and that said Letters Patent is hereby corrected as shown below:

Column 10,
Line 24, "$Het_1$" should read -- $Het_2$ --.
Line 35, "B=" should read -- X= --.
Line 46, "Ditrogen" should read -- nitrogen --.
Line 60, "ether" should read -- further --.

Column 12,
Line 53, "a most" should read -- almost --.
Lines 55 and 64, "$K^{30}$" should read -- $K^+$ --.

Column 13,
Line 4, "11 or 12" should read -- 12 or 13 --.

This certificate supersedes Certificate of Correction issued July 6, 2004 and August 29, 2006.

Signed and Sealed this

Twenty-eighth Day of November, 2006

JON W. DUDAS
*Director of the United States Patent and Trademark Office*